(12) United States Patent
Nishina et al.

(10) Patent No.: US 6,653,144 B1
(45) Date of Patent: Nov. 25, 2003

(54) METHOD AND AN APPARATUS FOR ANALYZING TRACE IMPURITIES IN GASES

(75) Inventors: Akira Nishina, Tokyo (JP); Tetsuya Satou, Tokyo (JP)

(73) Assignee: Nippon Sanso Corporation, Tokyo (JP)

( * ) Notice: Subject to any disclaimer, the term of this patent is extended or adjusted under 35 U.S.C. 154(b) by 0 days.

(21) Appl. No.: 09/491,101

(22) Filed: Jan. 25, 2000

(30) Foreign Application Priority Data

Jan. 25, 1999 (JP) ............................. 11-015421
Dec. 14, 1999 (JP) ............................. 11-354890

(51) Int. Cl.⁷ .................................................. G01N 33/00
(52) U.S. Cl. ......................... 436/161; 436/9; 436/141; 436/144
(58) Field of Search ................... 436/161, 9, 141, 436/144; 250/288, 281

(56) References Cited

U.S. PATENT DOCUMENTS 5,937,886 A * 8/1999 Girard et al. ............... 137/3

FOREIGN PATENT DOCUMENTS

| JP | 6-3461 | 1/1994 |
| JP | 6-74940 | 3/1994 |
| JP | 9-15207 | 1/1997 |

* cited by examiner

Primary Examiner—Jan Ludlow
Assistant Examiner—Sam P. Siefke
(74) Attorney, Agent, or Firm—Merchant & Gould P.C.

(57) ABSTRACT

The present invention relates to a method and an apparatus for analyzing trace impurities in gases, which enable to analyze a very small quantity of impurities by only a simple operation, without making the column arrangement or the structure of flow complicated. In the apparatus and the method, when the trace impurities are measured in ppb-sub ppb level by a combined analyzer which is equipped with an atmospheric pressure ionization mass spectrometer to the back of a gas chromatography, a mixed gas of various gases is used as a carrier gas or purified gases added to the gases outflowed from a gas chromatography.

2 Claims, 8 Drawing Sheets

METHOD AND AN APPARATUS FOR ANALYZING TRACE IMPURITIES IN GASES

BACKGROUND OF THE INVENTION

1. Field of the Invention

The present invention relates to a method and an apparatus for analyzing trace impurities in gases, and particularly to a method and an apparatus for detecting ppb—sub ppb level of trace impurities in various high-purified gases, by a combined analyzer comprised of gas chromatography and atmospheric pressure ionization mass spectrometer.

2. Description of the Prior Art

In case of analyzing (detecting) the impurities in high-purified gases by combined analyzer comprised of gas chromatography and atmospheric pressure ionization mass spectrometer, the outflowed gas(30–50 cc/min) from a gas chromatography which uses packed column, does not reach the gas flow(100–500 cc/min) necessary for a common atmospheric pressure ionization mass a spectrometer. Therefore, the outflowed gas from a gas chromatography was added by purified gases, the kind of which is the same with the carrier gas used in the gas chromatography, and then introduced into an atmospheric pressure ionization mass spectrometer(Japanese Patent Laid Open Gazette Hei. 6-3461 Japanese Patent Laid Open Gazette Hei.9-15207)

High-purified He(helium) or Ar gas is commonly used as the carrier gas and the purified gas. In particular, He is much preferred, because its ionization potential (24.59 eV) is higher than those of other gases, and all kinds of impurities except He can be detected.

Nevertheless, when He gas is used as a carrier gas, it is also sensitive to some main component such as $O_2$, $N_2$ and Ar, and their ions are generated in a large quantities. Therefore, some impurities hardly separable from the main components could not be detected well, and the measurement with a high sensitivity was hard to be obtained.

Under the circumstance, a method, in which impurities and main components are separated before being introduced into the atmospheric pressure ionization mass spectrometer, has been carried out to improved the sensitivity of measurement. For example, a complicated applied flow passage using a method such as "Heart Cut method", is installed and then cut just before the main component is outflowed from a gas chromatography, and the outflowed gas is introduced into the atmospheric pressure ionization mass spectrometer about at the point of time when the outflow of the main component ends.

However, there is a problem in the above method, in that the main components near the impurities were not separated well, and the introduction of the main components into the atmospheric pressure ionization mass spectrometer could not be avoided completely, which causes increased noises and weakened sensitivity when analyzing the impurities.

There is another problem that as columns used for a long-term could increase the retention time of the main components and thus the subject impurities could be separated and removed. Therefore, the retention time should be checked regularly, which requires much labors, and many columns for removing the main components and complicated flow are also required.

There is still another problem in another method of removing the main components by an absorbent, in that the subject impurities are removed together with the main components, or the other impurities are generated from the absorbent in ppb-ppm levels, resulting that the measurement in ppb level is hard to perform.

In addition, in case of using a atmospheric pressure ionization mass spectrometer, as He generates helium cluster ion ($He_4+$)(mass number=16) in a large amount, $CH_3+$(mass number=15) is measured for analyzing methane(M.W.=16). However, there is a problem that the sensitivity of mass number 15 is not so good as mass number 16($CH_4+$). Moreover, as the discharge of He is less stable compared with other gases and the stability of the main components are not good, the sensitivity to $H_2$, which is detected by $He_2H+$ (mass number=9) generated by combining $He_2+$ and proton, is also bad.

In case of Ar, which has a good discharge nature, there is a problem that the ionization potential of Ar(15.76 eV) is near that of $N_2$ (15.58 eV), and thus transfer of electric charges is hardly generated and the measurement of the impurities like $N_2$ or Ne, whose ionization potentials are higher than those of Ar, is impossible.

Under the circumstance, when the impurities are measured to the level of sub ppb in high purified $O_2$, He is used for Ne or $N_2$ of impurities, Ar is used for of $H_2$, $CH_4$, CO or $CO_2$ of impurities. That is, He should be supplied for analyzing $N_2$ etc., and Ar should be supplied for analyzing $H_2$ etc., as a carrier gas and purified gases added. Therefore, much labor and time were required for switching the supply of the gases, and the measurement cannot be carried out quickly.

The other method has been proposed, in which a third component gas is incorporated into the sample gas when the analysis is performed by atmospheric pressure ionization mass spectrometer alone (Japanese Patent Laid-Open Gazette Hei.6-7490). However, the method has a problem that the impurities in the third component gas should be checked in advance, because they could have an effect on the analysis of the impurities in the sample gas.

For example, when analyzing $N_2$ as an impurity in Ar, as the ionization potentials of both gases are mutually near each other, the sensitivity of the analysis is very bad and the measurement cannot be carried out at ppb level. Therefore, a method has been proposed, in which the measurement is performed by an atmospheric pressure ionization mass spectrometer using proton transfer rection after adding $H_2$ in the level of % into the sample gas of Ar. In this method, the check of the impurity $N_2$ in $H_2$ added, or the separation of CO in Ar both of which have the same mass number is hardly performed. Therefore, the measurement is carried out for $N_2$+CO, and thus the concentration of CO in the sample gas should be checked in advance, resulting in a very tedious and bothering work.

SUMMARY OF THE INVENTION

The present invention is purposed to provide a method and an apparatus for analyzing trace impurities in gases, which enable to analyze a very small quantity of impurities by a simple operation, without making the column arrangement or the structure of flow complicated.

In accordance with the object of the present invention, there is provided a method for analyzing the trace impurities in gases, the method comprising the steps of:

separating main components and trace impurities from a sample gas conveyed by a carrier gas by gas chromatography;

introducing the gases outflowed from said gas chromatography into an atmospheric pressure ionization mass spectrometer; and analyzing the trace impurities, wherein a mixed gas is used as the carrier gas.

In accordance with another object of the present invention, there is provided a method of analyzing the trace impurities in gases, the method comprising the steps of:

separating main components and trace impurities from a sample gas conveyed by a carrier gas by gas chromatography;

adding purified gas into the gases outflowed from said gas chromatography; introducing the gases into an atmospheric pressure ionization mass spectrometer; and analyzing the trace impurities, wherein a mixed gas is used as at least one of the carrier gas and the purified gas.

In accordance with still another object of the present invention, there is provided a method of analyzing the trace impurities in gases, the method comprising the steps of:

separating main components and trace impurities from a sample gas conveyed by a carrier gas by gas chromatography;

introducing the gases outflowed from said gas chromatography into an atmospheric pressure ionization mass spectrometer; and analyzing the trace impurities, wherein a single component gas is used as the carrier gas, and purified gas which are different from the carrier gas, are added to the outflowed gas.

In the above case, the method is characterized in that if said carrier gas is He, the added purified gas is Ar alone, or He—Ar mixed gas, or He—$H_2$ or Ar—$H_2$ mixed gas, and if said carrier gas is Ar, the added purified gas is He alone, or He—Ar mixed gas.

In accordance with still another object of the present invention, there is provided a method of analyzing the trace impurities in gases, the method comprising the steps of:

introducing a sample gas into a gas chromatography using He as a carrier gas;

separating main components and trace impurities from the sample gas;

adding a purified gas of Ar alone or Ar—He mixed gas into the gases outflowed from the gas chromatography;

introducing the gases into an atmospheric pressure ionization mass spectrometer; and analyzing the trace impurities, wherein the impurity of $H_2$ is detected by mass number 41 or 81, and the impurity of methane is detected by mass number 16.

In accordance with still further object of the present invention, there is provided a method of analyzing the trace impurities in gases, the method comprising the steps of:

introducing a sample gas into a gas chromatography using He as a carrier gas;

separating main components and trace impurities from the sample gas;

adding a purified gas into the gases outflowed from the gas chromatography;

introducing the gases into an atmospheric pressure ionization mass spectrometer; and analyzing the trace impurities, wherein at least two purified gases selected from i) He alone, ii) He—Ar mixed gas and iii) He—$H_2$ mixed gas or Ar—$H_2$ mixed gas, are selected and switchably used as said purified gas.

In accordance with still further object of the present invention, there is provided an apparatus for analyzing the trace impurities in gas, the apparatus comprising:

a gas chromatography for separating the main component and trace impurities from the sample gas conveyed by carrier gas;

an atmospheric pressure ionization mass spectrometer connected to the back part of the gas chromatography; and a purified gas adding passage for adding the purified gas outflowed from the gas chromatography, the purified gas adding passage being installed in a passage between the gas escaping part of the gas chromatography and the gas introduction passage of the atmospheric pressure ionization mass spectrometer, wherein i) a passage for supplying a purified gas whose kind is the same as the carrier gas, ii) a passage for supplying a purified gas whose kind is different from the carrier gas, and iii) mixed ratio regulating means installed in the purified gas adding passage for regulating a mixed ratio of both purified gases, and added amount controlling means installed in the purified gas adding passage for regulating the added amount of purified gases depending on the kind of the outflowed gas are further provided.

BRIEF DESCRIPTION OF THE DRAWING

For fuller understanding of the nature and objects of the invention, reference should be made to the following detailed description taken in conjunction with the accompanying drawing in which"

DETAILED DESCRIPTION OF THE PREFERRED EMBODIMENTS

Figure 1:
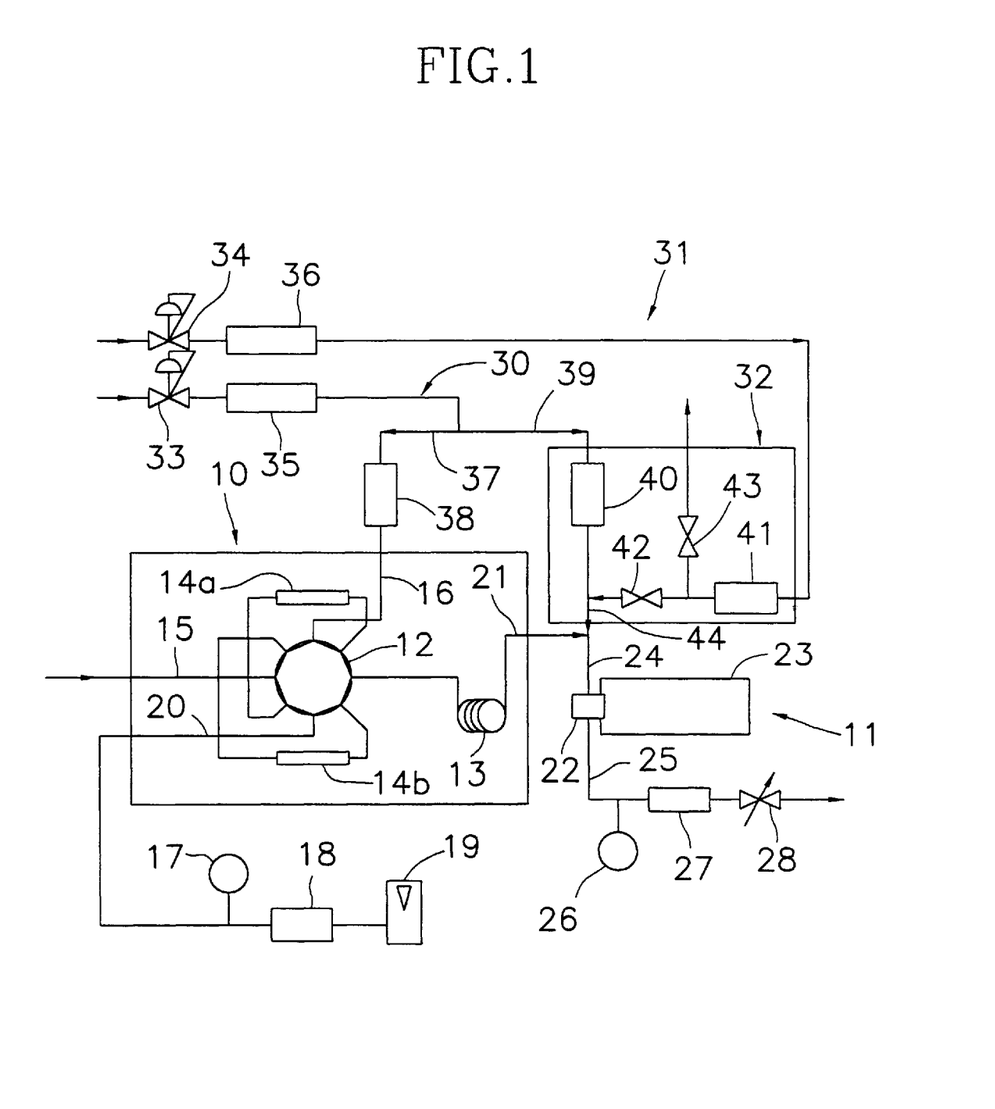
FIG. 1 is a flow diagram for showing a first example of the present apparatus.

FIG. 1 is a flow diagram for showing a first example of the present apparatus.

The apparatus is provided with i) a main purified gas supply system (30) for supplying a main purified gas for use as a purified gas to be added to the carrier gas of the gas chromatography(10) and a gas outflowed from the gas chromatography(10), ii) a sub-purified gas supply system(31) for supplying a sub-purified gas to be mixed with the main purified gas and then added to the outflowed gas, and iii) a purified gas supply regulating means(32) for regulating the supplied amount of the main purified gas and sub-purified gas to be added into the outflowed gas, together with iv) an atmospheric pressure ionization mass spectrometer(11) as a detecting part of a gas chromatography(10), which is installed in the back of the gas chromatography(10), for separating the main components and trace impurities from the sample gas.

The gas chromatography(10), formed by connecting i) a separating column(13) packed with a separator through an 8 way gas switching cock(12), ii) two sample loop(14a, 14b), iii) a sample gas introduction passage(15) connected to the sample gas source, iv) a carrier gas introduction passage(16) connected to the main purified gas supply system(30) and an exhaust passage(20) provided with a pressure gauge(17), a back pressure regulator(18) and a mass flow meter(19), serves to introduce the sample gas metered by a sample loop(14a,14b) into the separating column(13) by operating the 8 way gas switching cock(11), and to separate the respective components of the sample gas in the separating column(13) so that the components may be moved in order into the separated gas outflowing passage(21).

The atmospheric pressure ionization mass spectrometer (11) has an ion source part(22) and a mass separating part/detecting part(23), the ion source part(22) being connected with a gas introduction passage connected with the separated gas outflowing passage(21) and a gas escaping passage(25) for discharging the surplus gases. Further, the gas escaping passage(25) is provided with a pressure gauge (26) for maintaining the pressure of the ion source part(22), a back pressure regulator(27) and a mass flow meter(28).

The main purified gas supply system(30) and the sub-purified gas supply system(31) are provided with pressure regulators(33,34) and purifier(35,36) respectively. The main purified gas supply system(30) is diverged in two parts in the lower of the purifier(35), a passage(37) of the two parts is connected to the carrier gas introduction passage(16) of the gas chromatography(10) through the mass flow controller (38), whereas the other passage(39) of the two parts is connected to the purified gas supply regulating means(32). In addition, in the sub-purified gas supply system(31), the back of the purifier(36) is connected to the purified gas supply regulating means(32).

The purified gas supply regulating means(32), for mixing the main purified gas from the passage(39) and the sub-purified gas from the sub-purified gas supply system(31) in a fixed ratio, and for regulating the added amount into the outflowed gas, is provided with a mass flow controller for main purified gas(40) and a mass flow controller for sub purified gas(41), as well as a supply valve for controlling the supply of the sub-purified gas and a exhaust valve. The passage for discharging the purified gas after mixing(gas adding passage)(44) is connected in the way of the passage from the separated gas outflowing passage(21) to the gas introduction passage(24).

In addition, if an automatic controller(program controller) for controlling the flowing amount of the two mass flow controller and the opening/shutting of the valves(42,43) at the purified gas supply regulating means(32), the regulation of the mixed ratio of the purified gas or the added amount of the gas could be carried out automatically by connecting the controller with the operation of the gas chromatography(10).

As the purified gas and sub-purified gas, a single component gas such as He, Ar, $N_2$ and $H_2$, or a mixed gas such as He—Ar mixed gas, He—$H_2$ mixed gas, and Ar—$H_2$ mixed gas may be used. As a filler filled in the separating column, various filler such as molecular sieve type or Uni beads type can be used.

The following is an example of the processing to analyze trace impurities in a sample gas by using the above apparatus.

First, a mass flow controller or a back pressure regulator is set to a fixed value and the flow of the gases or the pressure in the system is set according to a required condition for the analysis. The sample gas is introduced from the sample gas introduction passage(15), and flowed into one of the sample loop (14a, 14b), for example the sample loop (14a), through the 8 way gas switching cock(12).

Then, if the 8 way gas switching cock(12) is operated so as to make the carrier gas flow into the sample loop(14a) in which the sample gas flows, the fixed amount of the sample gas metered in the sample loop(14a) is incorporated into the carrier gas and introduced into the separating column(13) where the components of the gas are separated in the dispersant as they proceed into the separating column(13), and outflowed from the separated gas outflowing passage (21) in a predetermined order.

The purified gas introduced from the gas adding passage (44) is added into the gas outflowed to the separated gas outflowing passage(the outflowed gas of the gas chromatography) in a fixed amount, and introduced into the ion source part(22) of the atmospheric pressure ionization mass spectrometer(11) through the gas introduction passage (24). The ion source part(22) is maintained to a predetermined pressure, such as 0.4 kg/cm$^2$(0.04 Mpa) by the back pressure regulator(27). Then, a part of the ionized gas after being introduced into the ion source part(22) passes through a slit and is introduced into the mass separating part/ detecting part(23), and the ion current of the respective components is detected after the separation of each mass.

As explained in the above, the impurities in the sample gas can be analyzed in a very sensitive and accurate way, by properly selecting the main purified gas and the sub-purified gas, and setting the added amount and the mixed ratio into the outflowed gas of the gas chromatography. In addition, as the components are separated in advance in the gas chromatography(10), even in the case that the added purified gases contain impurities, the kind of which is the same with the subject impurities to be analyzed, the peaks of the impurities in the sample gas can be clearly detected, and thus no prior check of the impurities in the purified gas is required, contrary to the conventional method in which only the atmospheric pressure ionization mass spectrometer is used.

The composition(mixed ratio) or the added amount of the purified gas to be added to the outflowed gas, can be set according to the main components of the sample gas, the impurities to be analyzed, the kinds of the main purified gas and the sub-purified gas and the like. In the above example, the mixed ratio can be selected by properly setting the flowing amount from both the mass flow controllers(40,41). Further, only the main purified gas may be added into the outflowed gas in a predetermined amount, by shutting off the supply valve(42) and opening the exhaust valve(43).

As above, the effect by the main components of the sample gas can be removed by adding a sub-purified gas different from the carrier gas. For example, in case the main purified gas is He, the sub-purified gas is Ar, and the main components of the sample gas are not only Ar but also $N_2$, almost all the $N_2$ in the main components would be removed by adding He—Ar mixed gas. In addition, in case the main component is $O_2$, as the reaction rate of $O_2$ is slower by about one digit and the effect by the main component is decreased as much, it would be possible to measure the impurities to a more accurate degree. In addition, the addition of Ar makes the discharge of the atmospheric pressure ionization mass spectrometer(11) more stable. Noises are reduced and the base lines are also stabilized.

In addition, in case of using He as a main purified gas and Ar as a sub-purified gas, as the carrier gas could be He, the separating column(13) of the gas chromatography(10) gets more stable. Further, by adding He—Ar mixed gas into the outflowed gas, the $H_2$ impurities, which has been detected by mass number 9, can be detected by mass number 41 or 81, and methane, which has been detected by mass number 15, can be detected by mass number 16, and thus the sensitivity of the detection can be markedly improved.

That is, in case of adding He—Ar mixed gas, the generated $He_4+$ can be destroyed and the background can be reduced, and it can be possible to measure the methane of impurity by mass number 16. At the same time, in case of using Ar in which case Ar+ or $Ar_2+$ becomes the main reactant, the detection of impurities $H_2$ could be possible by mass number 41(ArH+) or mass number 81($Ar_2H+$) with less noise, instead of the detection by the mass number 9($He_2H+$) with greater noise.

In case of using He as a main purified gas, and Ar as a sub-purified gas, by switching the gases added to the outflowed gas with He alone and He—Ar mixed gas, the impurities undetectable by adding a mixed gas, such as $N_2$, Ne, Ar, etc., can be detected by He alone, while the scope of the subject components detectable can be enlarged and the sensitivity can be improved. Further, as the main purified gas of He can be also used as a carrier gas, the labor and time for changing a carrier can be saved. Besides, the amount of the purified gas added to the outflowed gas can be increased or decreased according to the kinds of the outflowed gases from the gas chromatography(10).

In case of using He and Ar, the ratio of Ar to He can be established freely. If the carrier gas is He, the concentration of the Ar in the added gas is preferably settled to be 0–50%.

In addition, in case of measuring impurities of $N_2$ in Ar, for which many steps of work are needed up to now, the effect of $N_2$ impurity in $H_2$ can be ignored, by using a $H_2$-contained mixed purified gas as a mixed gas to be added after being separated by gas chromatography, without introducing $H_2$ into the sample gas in the ion source part of the atmospheric pressure ionization mass spectrometer, such as He—$H_2$ mixed gas or Ar—$H_2$ mixed gas; and the $N_2$ impurity in Ar can be discriminated and measured in detail, because the CO and $N_2$ can be separated by the gas chromatography. Moreover, as a $H_2$—added method, a $H_2$-contained mixed gas can be used as a carrier gas, or the improved sensitivity can be expected by adding $H_2$ in measuring impurities, the sensitivity of which can be increased by using proton transfer reaction.

As the gas chromatography(10) or the atmospheric pressure ionization mass spectrometer(11), the conventional ones can be used. Moreover, the scope of the main components of the sample and the impurities to be analyzed are not limited specifically; not only the highly purified gas such as $O_2$, $N_2$, $H_2$, Ar, He, Xe, Kr, and the like but also the gases used as material for a semiconductor can be applied for this analyzing method. Further, it is possible to add a purified gas comprising of 3 and more components, for example He, Ar and Ne, into the outflowed gas.

Figure 2:
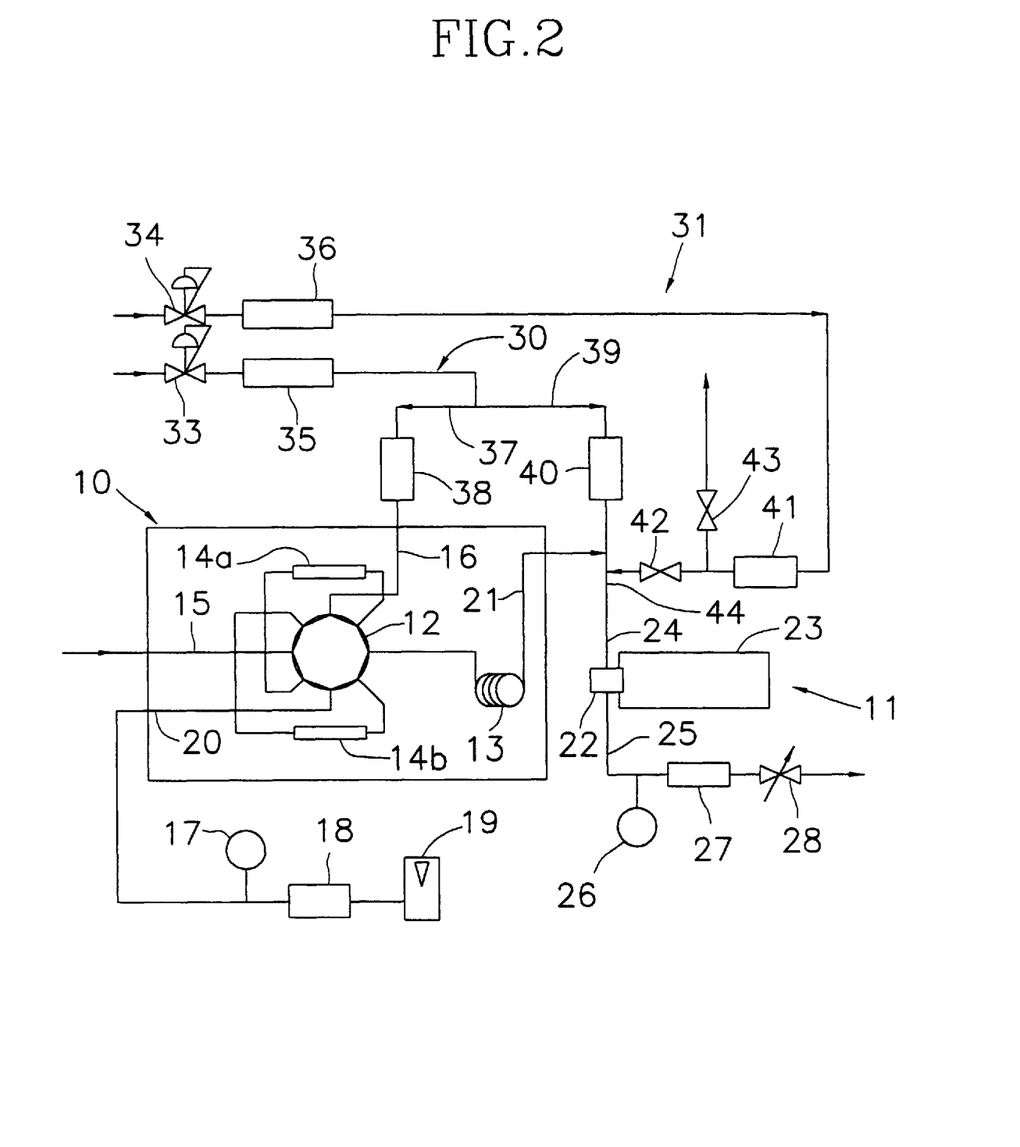
FIG. 2 is a flow diagram for showing a second example of the present apparatus.

FIG. 2 is a flow diagram for showing a second example of the present apparatus. In this analyzing apparatus, the gas outflowed into the separated gas outflowing passage(21), is added by the main purified gas in a predetermined amount, and then added by the sub-purified gas in the back. Like in the above case, the purified gas can be added into the outflowed gas in a desired amount or in a desired mixed ratio, by controlling the flow of the both mass flow controllers(40,41) or by opening or shutting the valves(42, 43).

As the other parts of the apparatus can be organized as in the first example, the same numbers will be given to the same constitutions, without repeating the detailed explanation (It will be the same in the other examples in the following).

Figure 3:
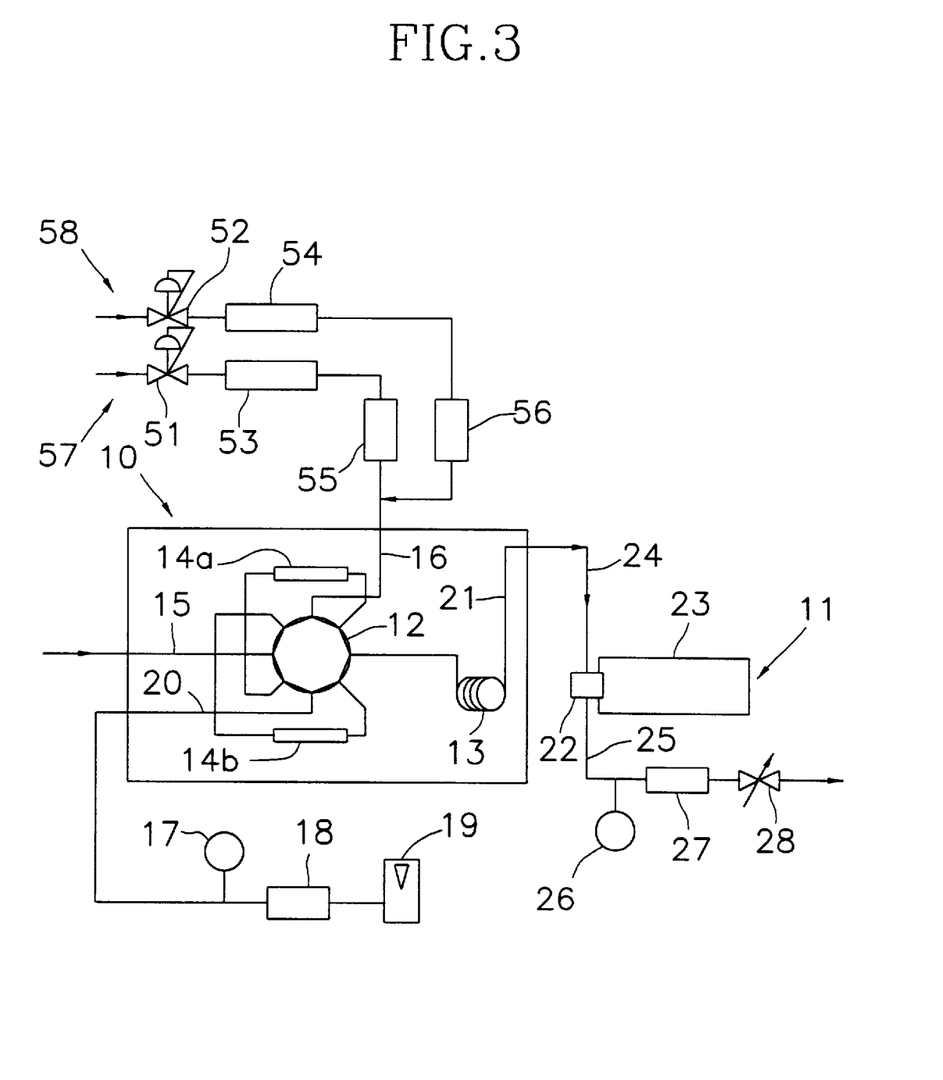
FIG. 3 is a flow diagram for showing a third example of the present apparatus.
Figure 4:
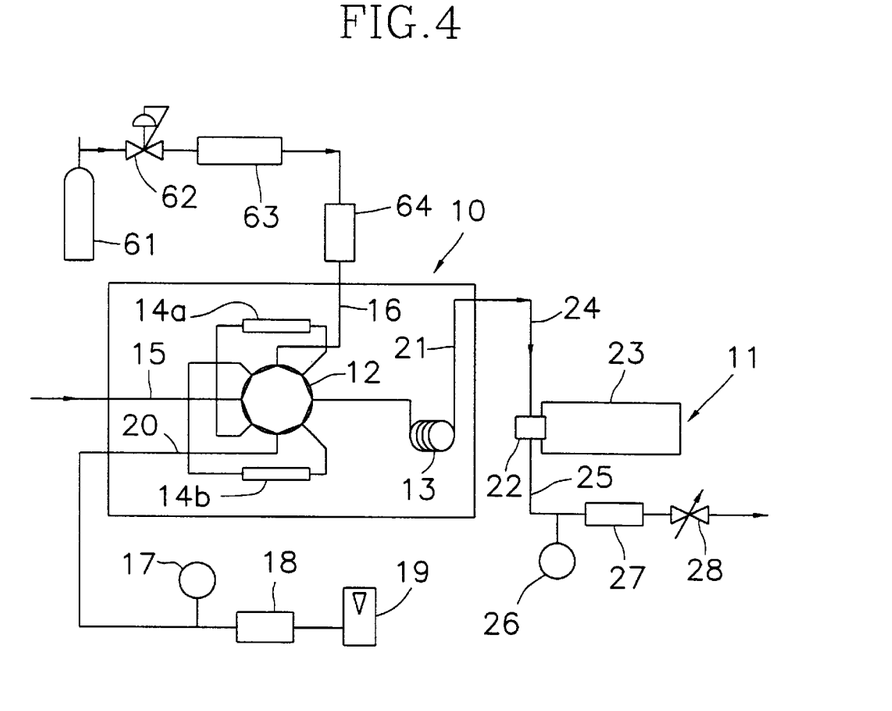
FIG. 4 is a flow diagram for showing a fourth example of the present apparatus.

FIG. 3 and FIG. 4 are flow diagrams showing the third and fourth examples of the present apparatus. The examples show apparatuses by which the amount of the outflowed gas from the gas chromatography(11) can be increased to a minimum amount commonly required for the atmospheric pressure ionization mass spectrometer; or a minimum amount of the gas of the atmospheric pressure ionization mass spectrometer(11) can be decreased to the common amount of the outflowed gas from the gas chromatography (10); or the analysis can be performed by the atmospheric pressure ionization mass spectrometer(11) without adding the purified gas into the outflowed gas from the gas chromatography(10).

In the apparatus of the third example, the main purified gas supply system (57) and the sub-purified gas supply system (58), which have the pressure regulators(51,52), the purifiers(53,54) and mass flow controllers (55,56) respectively, are connected to the carrier gas introduction passage(16) of the gas chromatography(10), so that one of the main purified gas and the sub-purified gas, or the mixed gases of the main purified gas and the sub-purified gas in an appropriate ratio, can be supplied as a carrier gas.

In the analyzing apparatus like the above, the most appropriate carrier gas can be selected and used, depended on the kinds of the main components of the sample gas or the impurities to be measured; and a high sensitive detection can be performed by selecting the gases which are properly mixed according to the outflow timing of the subject impurities.

Further, in the apparatus of FIG. 4, the mixed gases in a fixed ratio are filled into the gas cylinder(61), which is connected to the carrier gas introduction passage(16) through the pressure regulator(62), purifier63) and mass flow controller(64). That is, if the subject sample gas to be analyzed is determined, the predetermined mixed gas is to be supplied from the gas cylinder(61), such that the apparatus can be simplified without diminishing of the accuracy of the analysis. Further, as a purifier(63) for refining the mixed gas, a purifier of getter type is recommended.

EXAMPLE 1

The impurities contained in $O_2$ gas($H_2$, methane, $N_2$, CO, $CO_2$) was measured by using the apparatus of the FIG. 1. As the gas chromatography, Uni beads 1S was filled for measuring $CO_2$, and molecular sieve 13×S was filled for measuring others, into the separating column which had a diameter of 4 mm and a length of 2 m and was made from stainless steel. The obtained amount of the sample gas was 3 cc, and the flow amount of the carrier(main purified gas) of He was 42 cc/min.

As for the measurement of $N_2$, was performed, after He was added into the outflowed gas in 1000 cc/min. Then, after the amount of the gas added to the outflowed gas was changed to 328 cc/min and Ar(sub-purified gas) was added to He, the measurements of $H_2$, methane, CO and $CO_2$ were performed while changing the Ar concentration in the range of 0–90%. The relations between the Ar concentration and the intensities of the peaks of the respective impurities are shown in FIG. 5.

Figure 5:
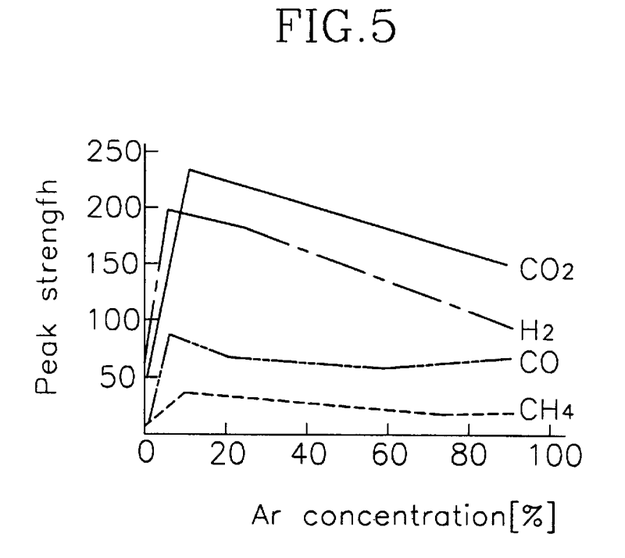
FIG. 5 is a diagram for showing the relation between the concentration of Ar and the peak intensity of the respective impurities in the first example.

As apparent in FIG. 5, the intensities of the peaks in the Ar-added case were higher than in the Ar-free case(Ar concentration=0), in all the cases.

Figure 6:
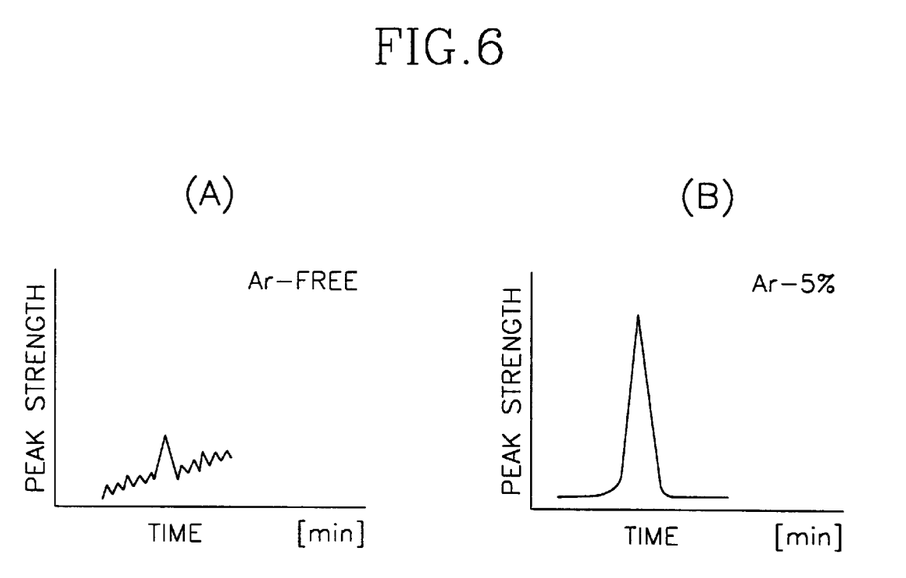
FIG. 6 is a drawing for comparing the peaks of methane according to the existence of Ar of the first example.
Figure 7:
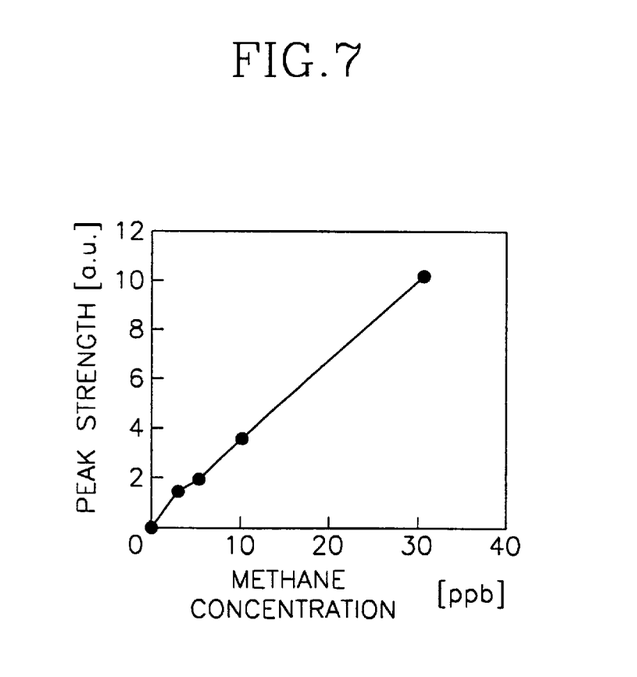
FIG. 7 is a diagram for showing the calibration curve, in the case of adding Ar of the first example.

In addition, FIG. 6 shows the measured peaks in the Ar-free case(FIG. 6(a)) and in 5% Ar concentration case (FIG. 6(b)), for the measurement of methane. It is recognized that if Ar is added, the noises of the background were decreased and the base line became stabilized. FIG. 7 shows the calibration curve of methane in Ar-added cases, in which the obtained linearity was satisfactory and the accuracy was also high enough.

The result was that in case of using He—Ar mixed gas(Ar concentration=5%), the detection limit value of $H_2$ in $O_2$ gas(S/N=2, the same in the following) was 0.5 ppb, that of methane was 0.2 ppb and that of CO was 0.3 ppb. In case of Ar-free, the detection limit value was 2 ppb for $H_2$, 2 ppb for methane, 1 ppb for CO and 0.5 ppb for $N_2$.

When measuring the impurities of the high purified $O_2$ gas ($\geq$99.99995%), the result was 1 ppb for $H_2$, less than 0.3 ppb for methane, 1.5 ppb for CO and 11 ppb for $N_2$. In this method in which the kind of the carrier was not changed and the gas added to the outflowed gas was switched with He alone and He—Ar mixed gas(Ar 5%), the analysis of impurities of 4 component was carried out successfully in a short period of time of 30 minutes in a sub-ppb level.

EXAMPLE 2

Figure 8:
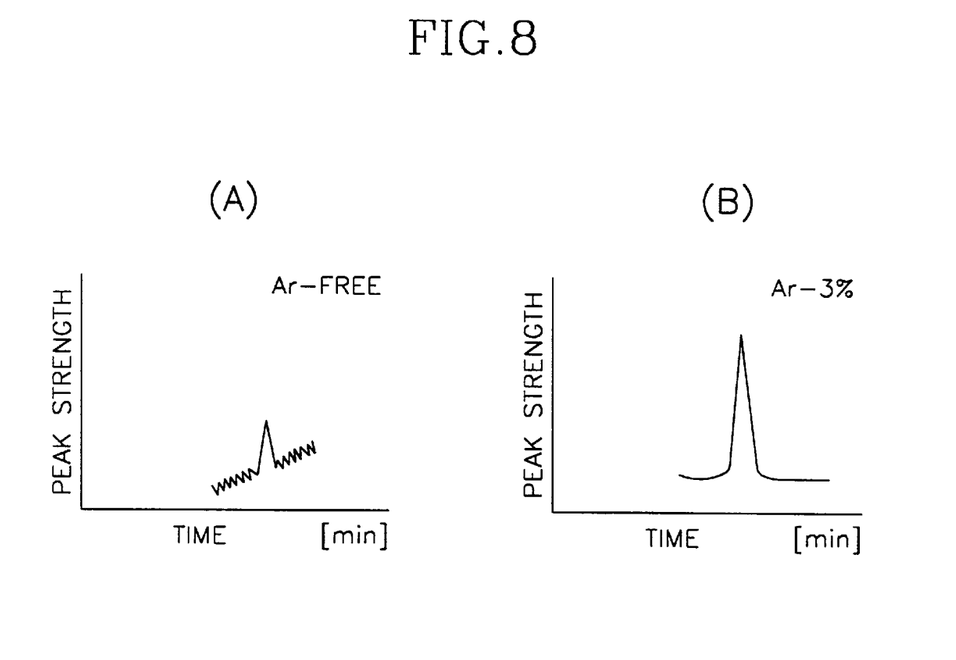
FIG. 8 is a drawing for comparing the peaks of CO according to the existence of Ar of the second example.

The operation was carried out in almost the same condition with the EXAMPLE 1, except that the subject impurities to be measured was CO, and the total amount of the gases added to the outflowed gas was 420 cc/min. FIG. 8 shows the measured peaks for the Ar-free case (FIG. 8(a)) and for the case of 3% of Ar concentration(FIG. 8(b)).

Figure 9:
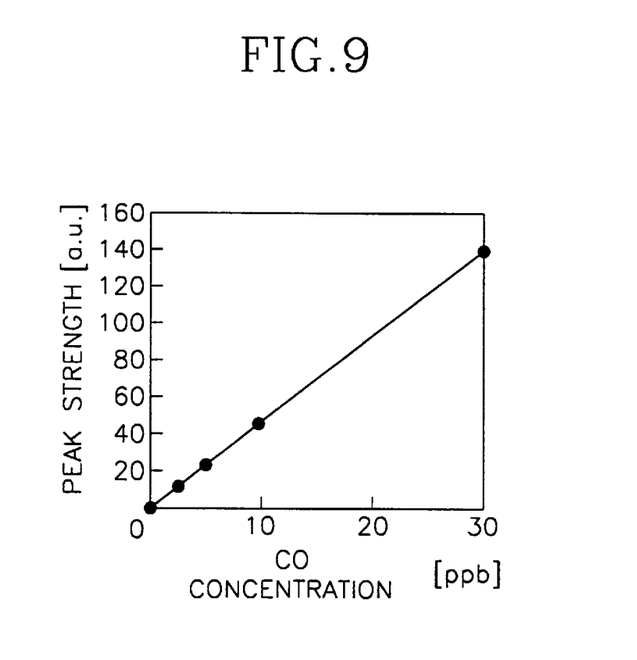
FIG. 9 is a diagram for showing the calibration curve of CO, in the case of adding Ar of the second example.

As apparent in FIG. 8, the peak in the case of 3% of Ar was stronger and more stable in the base line compared with the cases of Ar-free. FIG. 9 shows a calibration curve for the case of 3% of Ar concentration. From the above, the detection limit of CO was 0.3 ppb.

EXAMPLE 3

The measurement of $CO_2$ in $N_2$ was carried out in the apparatus of FIG. 1, by using Ar as a main purified gas and He as a sub-purified gas. The separating column had 4 mm of diameter and 1 m of length, and was made from stainless steel, being filled with Uni beads 1S. The obtained amount of the sample gas was 4 cc, and the flow of the carrier gas was 112 cc/min.

The measurement of $CO_2$ was carried out for the He-free case(FIG. 10(a)) and for the case that the He concentration was 50% in the purified gas(FIG. 10(b)), while the amount of the gases added to the outflowed gas was 420 cc/min.

Figure 10:
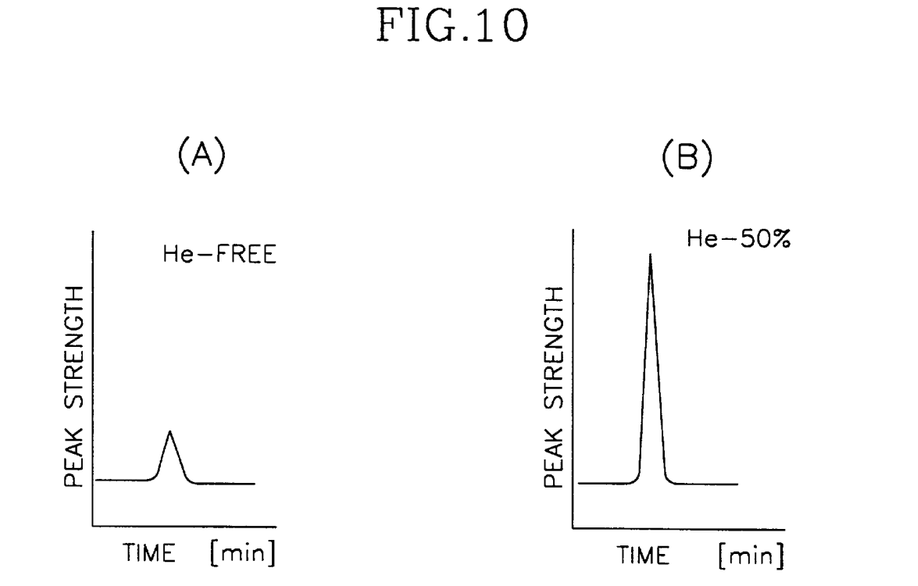
FIG. 10 is a drawing for comparing the peaks of CO according to the existence of He of the third example.

As apparent in FIG. 10, the intensity of the peak has become several times higher by adding He. Further, the detection limit of the case of Ar alone was 0.6 ppb, while the detection limit was improved to 0.2 ppb by adding Ar with 50% of He concentration into the outflowed gas.

EXAMPLE 4

The measurement of $CO_2$ in $N_2$ gas was carried out by using the apparatus showed in FIG. 3.

The separating column of the gas chromatography had 4 mm of diameter and 2 m of length and was made from stainless steel, being filled with molecular sieves 13×S. The obtained amount of the sample gas was 5 cc, and the flow of the carrier gas was 112 cc/min.

A mixed purified gas(Ar concentration=about 2%), in which 2 cc of Ar was mixed to 110 cc of He, was used as a carrier gas. The temperature of the separating column was 35° C. For the atmospheric pressure ionization mass spectrometer, the slit diameter was set to be small and the outlet valve was regulated, so that the inside of the ion source part may not fall under the atmospheric pressure, even in the case that the purified gas is not supplemented to the outflowed gas from the gas chromatography.

As a result of the above, the detection limit of $CO_2$ was improved to 0.5 ppb by adding Ar, compared with the case that the limit was 5 ppb when He alone was used as a carrier gas.

EXAMPLE 5

The measurement of $N_2$ in Ar was carried out by using the apparatus of FIG. 1. The separating column of the gas chromatography had 4 mm of diameter and 2 m of length and was made from stainless steel, being filled with molecular sieve 13×S. The obtained amount of the sample gas was 3 cc, and the flow of the carrier gas (main purified gas) was 42 cc/min, in which He was used as a carrier gas.

He—$H_2$ mixed gas was used as the gas added to the outflowed gas, and the $H_2$ contents were set to be in the range of 0.05–0.4%. The added amount of the mixed gas was determined so that the amount of the gas introduced into the atmospheric pressure ionization mass spectrometer is 500 cc/min.

Figure 11:
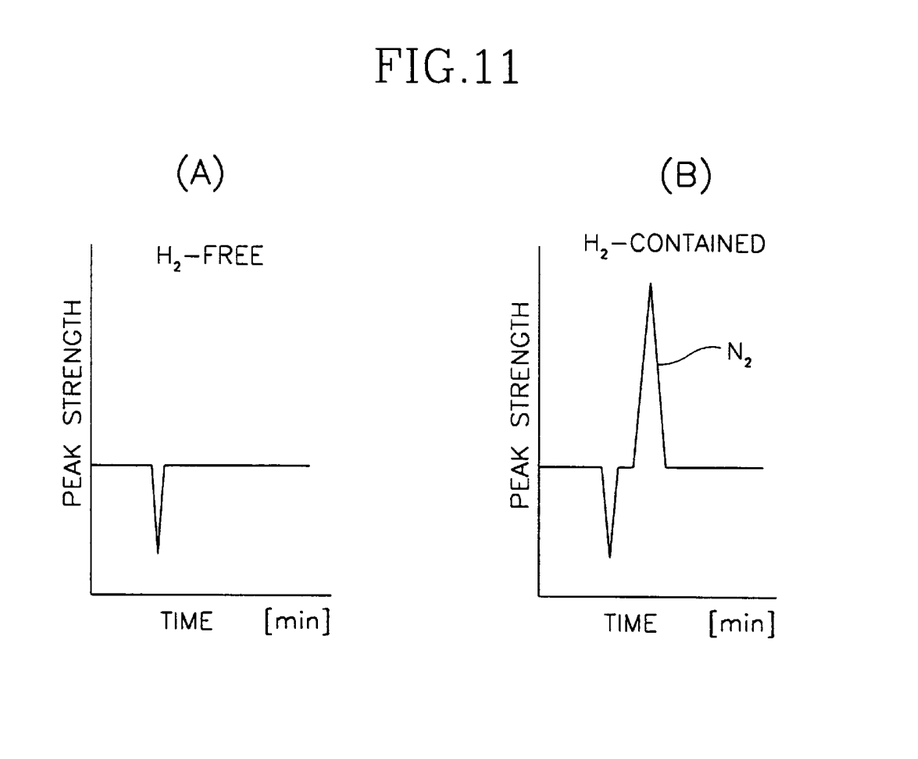
FIG. 11 is a diagram for comparing the peaks of $N_2$, in the case of adding $H_2$ of the fifth example.

As for analyzing $N_2$, the measured result of $H_2$ free case is shown in FIG. 11(a) and that of $H_2$-added case is shown in FIG. 11(b). As apparent in both figures, $N_2$, which was never detected in $H_2$-free case, was detected as $N_2$-H+ (mass number=29) by a proton transfer reaction resulted from the addition of $H_2$.

Figure 12:
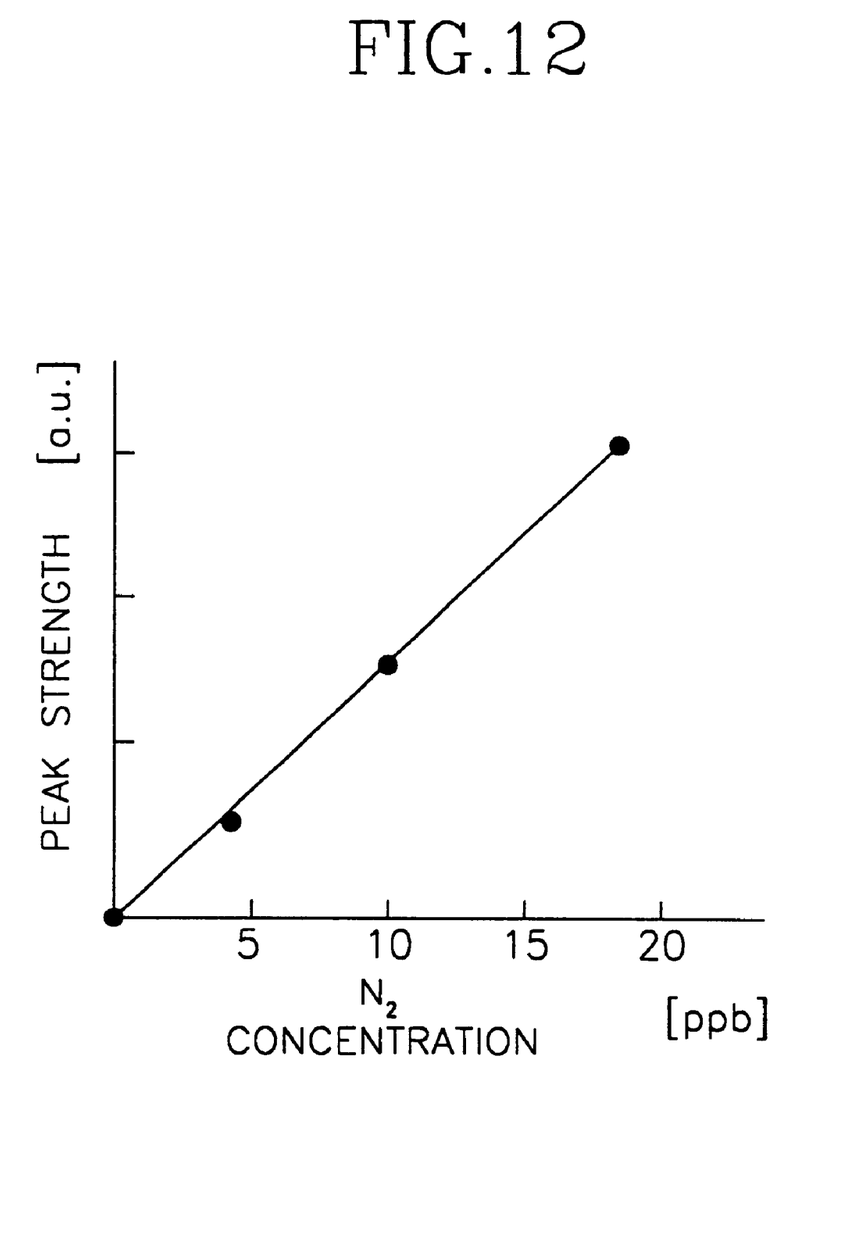
FIG. 12 is a diagram for showing the calibration curve of $N_2$, in the case of adding $H_2$ of the fifth example.

Moreover, as shown in FIG. 12, the calibration curve line of the $H_2$-added case was satisfactory. In the result of the measurement, when the mixed gas(He+0.05% of $H_2$) was used as an added gas, the detection limit of $N_2$ in Ar was 1 ppb.

In addition, when the amount of $N_2$ contained in Ar in a high purified Ar gas cylinder was measured, 72 ppb of $N_2$ was detected. Further, when $N_2$ was measured after being purified through getter type purifier, the $N_2$ amount was less than 1 ppb.

As explained in the above, the present method has made it possible for the trace impurities in various gases to be detected in a sensitive and detailed way, and to be analyzed in ppb-ppt levels in a short period of time, without the requirement of the complicated operation and constitution of the apparatus.

What is claimed is:

1. A method for analyzing trace impurities in gases, the method comprising the steps of:

introducing a sample gas into a gas chromatography using He as a carrier gas;

separating main components and trace impurities from the sample gas;

adding a purified gas of Ar alone or Ar—He mixed gas into the gases outflowed from the gas chromatography;

introducing the gases into an atmospheric pressure ionization mass spectrometer; and analyzing the trace impurities, wherein the impurity of $H_2$ is detected by mass number 41 or 81, and the impurity of methane is detected by mass number 16.

2. A method according to claim 1, characterized in that the added amount of the purified gases is changed depending on the kind of the outflowed gas.

* * * * *